(12) United States Patent
Zhang (10) Patent No.: US 9,211,333 B2
(45) Date of Patent: Dec. 15, 2015

(54) ANTI-CANCER AGENTS SYNTHESIZED BASED ON MILIUSANE COMPOUNDS

(71) Applicant: Hong Kong Baptist University, Hong Kong (HK)

(72) Inventor: Hongjie Zhang, Hong Kong (HK)

(73) Assignee: HONG KONG BAPTIST UNIVERSITY, Kowloon Tong, Kowloon (HK)

( * ) Notice: Subject to any disclaimer, the term of this patent is extended or adjusted under 35 U.S.C. 154(b) by 0 days.

(21) Appl. No.: 13/831,997

(22) Filed: Mar. 15, 2013

(65) Prior Publication Data

US 2013/0324580 A1 Dec. 5, 2013

Related U.S. Application Data

(60) Provisional application No. 61/655,990, filed on Jun. 5, 2012.

(51) Int. Cl.

| A61K 45/06 | (2006.01) |
| --- | --- |
| A61K 31/4025 | (2006.01) |
| A61K 31/343 | (2006.01) |
| C07D 405/12 | (2006.01) |
| C07D 307/94 | (2006.01) |
| C07D 407/06 | (2006.01) |
| C07D 409/12 | (2006.01) |

(52) U.S. Cl.
CPC ............... *A61K 45/06* (2013.01); *A61K 31/343* (2013.01); *A61K 31/4025* (2013.01); *C07D 307/94* (2013.01); *C07D 405/12* (2013.01); *C07D 407/06* (2013.01); *C07D 409/12* (2013.01)

(58) Field of Classification Search
USPC ................. 514/409, 462; 548/407; 549/265
See application file for complete search history.

(56) References Cited

U.S. PATENT DOCUMENTS

2009/0318548 A1 12/2009 Plourde et al.
2011/0021624 A1 1/2011 Nan et al.

FOREIGN PATENT DOCUMENTS

WO 2011098433 A1 8/2011

OTHER PUBLICATIONS

Cancer [online], [retrieved on Jul. 6, 2007] Retrieved from the Internet, URL: http://www.nlm.nih.gov/medlineplus/cancer.html.*
Lala et al., Role of nitric oxide in tumor progression: Lessons from experimental tumors, Cancer and Metastasis Reviews (1998), 17, 91-106.*
Golub et al., Molecular Classification of Cancer: Class Discovery and Class Prediction by Gene Expression Monitoring, Science (1999), vol. 286, 531-537.*
Zhang et al., "Miliusanes, a class of cytotoxic agents from Miliusa sinensis." Journal of Medicinal Chemistry 2006; 49: 693-708.
WHO: http://www.who.int/mediacentre/factsheets/fs297/en/index.html; retrieved on Apr. 28, 2012.

* cited by examiner

*Primary Examiner* — Kristin Vajda
(74) *Attorney, Agent, or Firm* — Ella Cheong Hong Kong; Sam T. Yip (57) ABSTRACT

The present invention is in the field of pharmaceuticals and chemical industries. In particular, the present invention relates to new anticancer agents based on miliusane compounds. The present invention also includes its preparation and application method for treating cancer.

10 Claims, 4 Drawing Sheets

| | Benzoylmiliusol (BZmiliusol) | o-Methoxy-BZmiliusol | m-Methoxy-BZmiliusol | p-Methoxy-BZmiliusol | o-Dimethoxy-BZmiliusol | m-Dimethoxy-BZmiliusol | Trimethoxy-BZmiliusol |
|---|---|---|---|---|---|---|---|
| KB: | 2.90 | 0.96 | 4.32 | 0.45 | 0.87 | 0.92 | 0.70 |
| Col2: | 3.56 | 1.71 | 2.39 | 0.75 | 0.79 | 1.05 | 1.22 |
| Lu1: | 5.70 | 0.89 | 8.06 | 0.70 | 0.80 | 0.73 | 0.57 |
| LNCaP: | 2.51 | 2.37 | 4.32 | 1.31 | 0.45 | 0.80 | 0.49 |
| MCF-7: | 5.13 | 0.94 | 3.47 | 0.45 | 0.46 | 0.84 | 0.49 |

| | o-Fluoro-BZmiliusol | p-Chloro-BZmiliusol | o-Dichloro-BZmiliusol | p-Iodo-BZmiliusol | Undecanoyl-miliusol | Cyclohexane-carboxyloylmiliusol | Thiophene-carboxyloylmiliusol |
|---|---|---|---|---|---|---|---|
| KB: | 0.87 | 1.09 | 0.36 | 1.00 | 1.52 | 1.49 | 2.19 |
| Col2: | 1.14 | 0.63 | 0.43 | 1.43 | 0.84 | 1.73 | 2.16 |
| Lu1: | 1.78 | 1.05 | 0.37 | 1.62 | 0.78 | 1.17 | 2.73 |
| LNCaP: | 1.59 | 1.89 | 0.36 | 1.98 | 1.07 | 1.19 | 3.30 |
| MCF-7: | 1.11 | 0.68 | 0.52 | 0.73 | 0.77 | 1.12 | 1.56 |

| | m-Chloro-BZmiliusol | p-Chloro-BZmiliusol | p-Iodo-BZmiliusol | o-Bromo-BZmiliusol | o-Methoxy-BZmiliusol | p-Methoxy-BZmiliusol | Methoxyacetyl-miliusol |
|---|---|---|---|---|---|---|---|
| KB: | 3.72 | 2.42 | 2.23 | 8.62 | 2.15 | 1.00 | 16.36 |
| Col2: | 13.61 | 1.20 | 2.73 | 6.77 | 3.26 | 1.44 | 15.61 |
| Lu1: | 20.99 | 2.08 | 3.22 | 15.39 | 1.78 | 1.39 | 25.27 |
| LNCaP: | 9.66 | 8.30 | 8.69 | 16.30 | 10.39 | 5.73 | >26.6 |
| MCF-7: | 9.10 | 1.43 | 1.52 | 3.50 | 1.96 | 0.94 | 1.70 |

FIGURE 4 (Prior Art)

ANTI-CANCER AGENTS SYNTHESIZED BASED ON MILIUSANE COMPOUNDS

CROSS-REFERENCE TO RELATED APPLICATIONS

The present application claims priority of U.S. provisional application No. 61/655,990 filed Jun. 5, 2012, and which the disclosure is hereby incorporated by reference by its entirety.

FIELD OF INVENTION

The present invention is in the field of pharmaceuticals and chemical industries. In particular, the present invention relates to new anticancer agents based on the miliusane compounds. The present invention also includes its preparation and application method for treating cancer.

BACKGROUND OF INVENTION

Cancer, in one form or another, is a leading cause of death, and claimed the lives of more than 7.6 million people worldwide in 2008, according to the compiled statistics by WHO (WHO: http://www.who.int/mediacentre/factsheets/fs297/en/index.html; retrieved on 28 Apr., 2012). It is estimated that the annual death toll will reach 13.1 millions by 2030. Although numerous cancer chemotherapeutics are available today, they often have very narrow therapeutic indices and very severe side effects. In addition, cancers can and often do develop resistance to many of these drugs. The fact that there currently are no drugs available that are capable of curing cancer diseases, the discovery and development of new anti-cancer drugs are very much needed and the undertaking of such studies is imperative.

Figure 1:
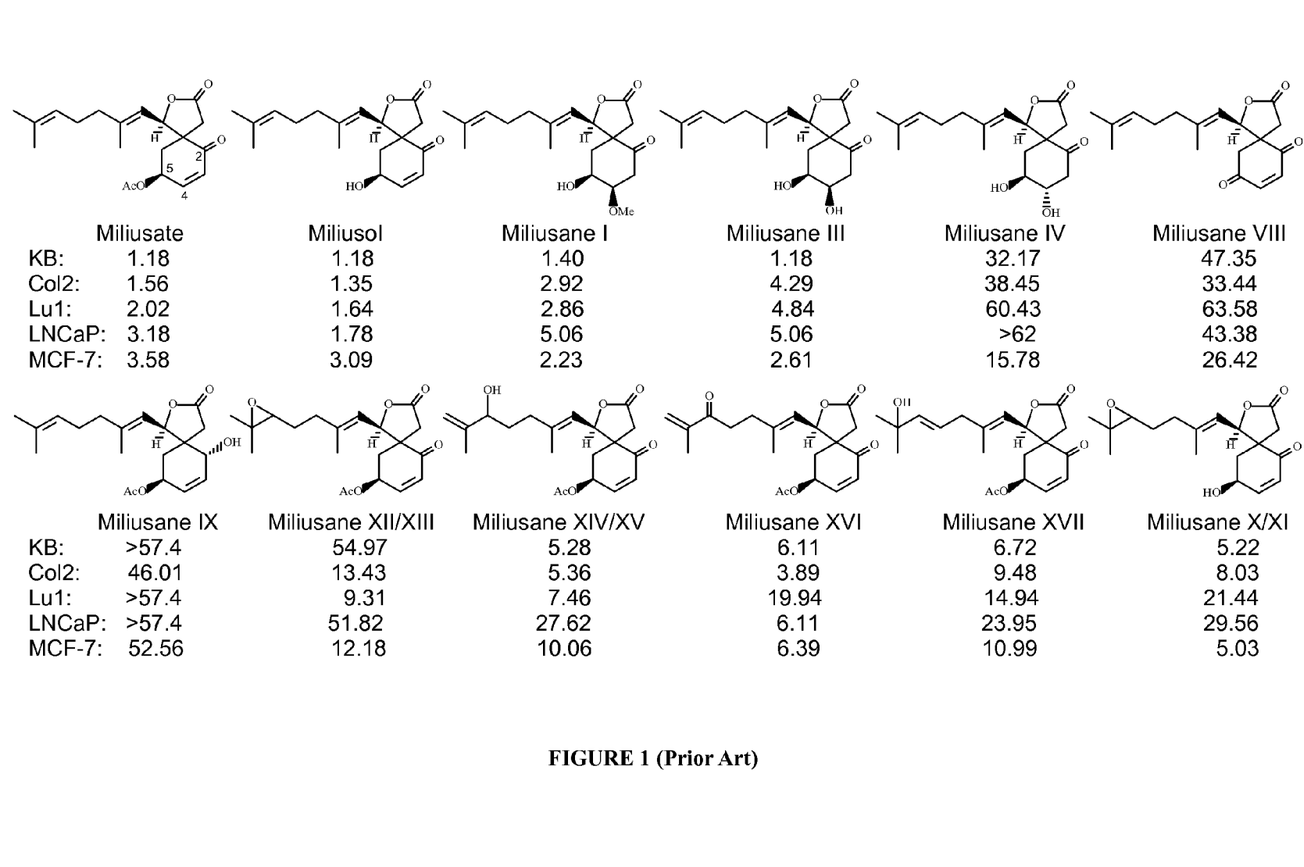
FIG. 1 shows tumor cell killing activity of miliusanes (vinblastine: KB=0.00037, Lu1=0.011, Col2=0.0043, LNCaP=0.00061, MCF-7=0.0026). The results are expressed as $IC_{50}$ in μM.

In a continuing drug discovery program, over 8,000 plant and microbial extracts for anticancer activity have been evaluated using a panel of cancer cell lines, resulting in the discovery of dozens of active lead molecules. Among these active leads are a series of promising compounds belonging to a cluster of novel molecules with a rare C-18 skeleton, which we designated collectively as "miliusanes". These compounds were isolated from the leaves, twigs and flowers of *Miliusa sinensis* Finet and Gagnep. (Annonaceae) through bioassay-guided fractionation. Of the 22 miliusane isolates, 20 are new molecules. Ten of these compounds demonstrated tumor cell killing activity in a panel of cell lines (see FIG. 1) (Zhang H J, Ma C Y, Hung N V, Cuong N M, Tan G T, Santarsiero B D, Mesecar A D, Soejarto D D, Pezzuto J M, Fong H H S. Miliusanes, a class of cytotoxic agents from *Miliusa sinensis*. Journal of Medicinal Chemistry 2006; 49: 693-708).

Miliusol

Miliusate

Miliusane I

Figure 2:
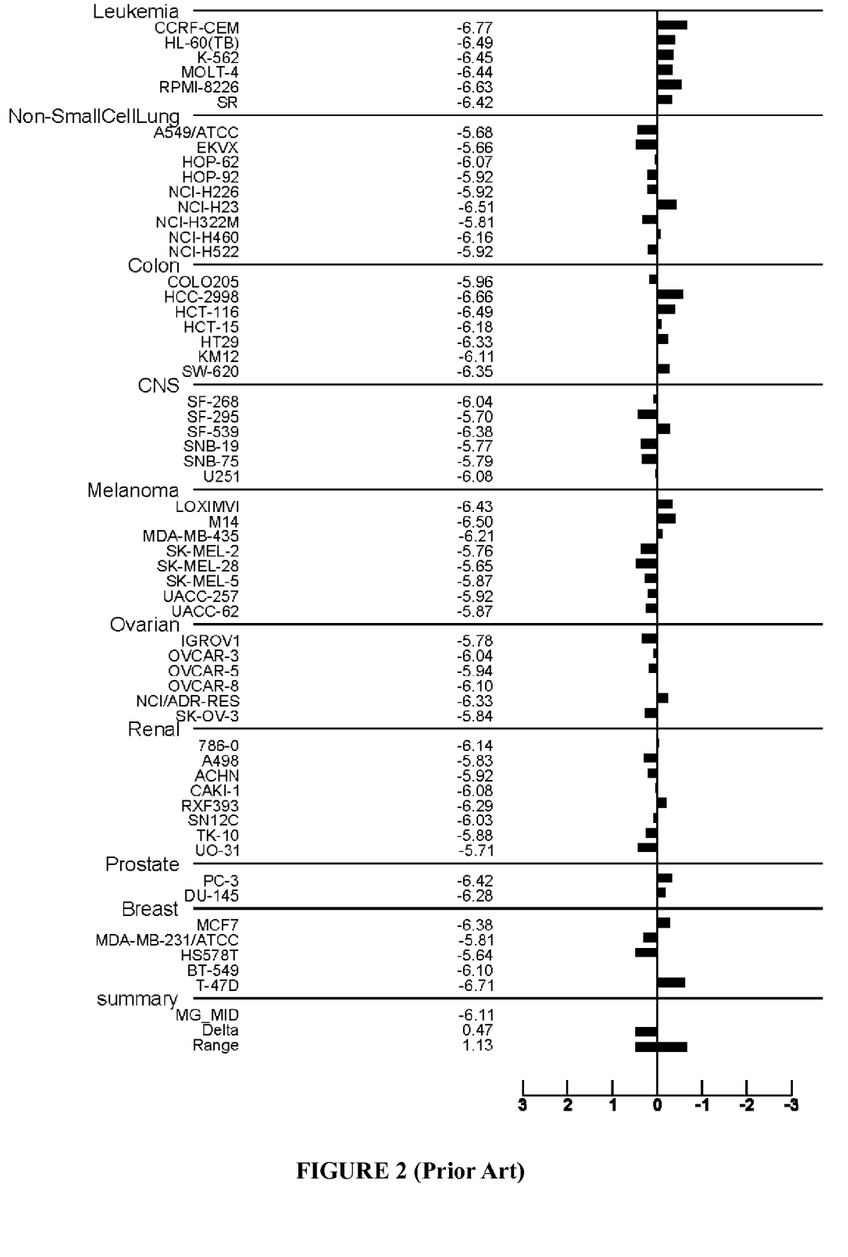
FIG. 2 The NCI 60 cell line data of miliusol. The $\log(GI_{50})$ values of miliusol against the NCI 60 tumor cell lines [$GI_{50}$ is the concentration in molarity (M) required to inhibit cell growth by 50%].
Figure 3:
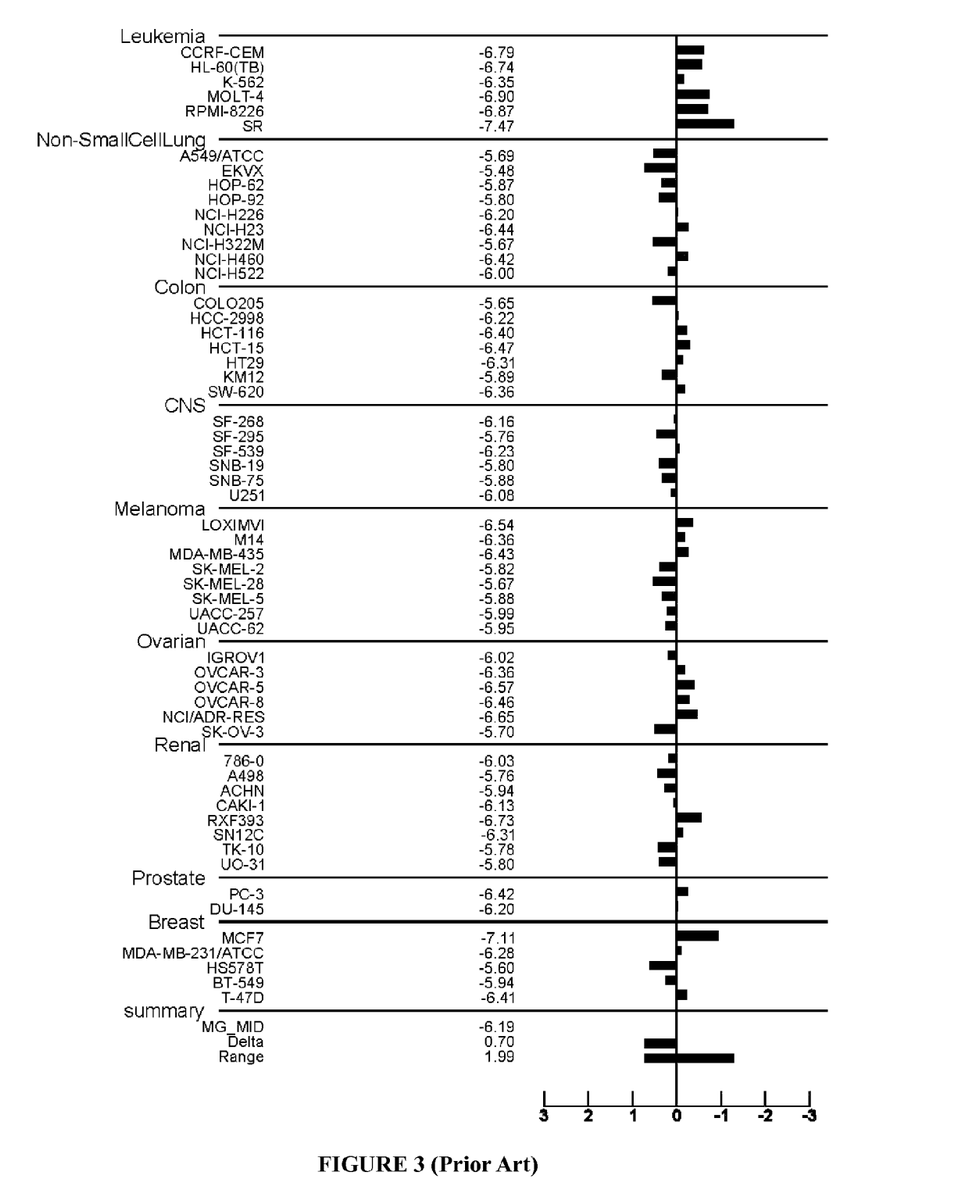
FIG. 3 The NCI 60 cell line data of miliusate. The $\log(GI_{50})$ values of miliusate against the NCI 60 tumor cell lines [$GI_{50}$ is the concentration in molarity (M) required to inhibit cell growth by 50%].

Miliusol, miliusate as well as miliusane I were further evaluated in the NCI 60 cell line panel (see FIGS. 2 and 3). The mean $GI_{50}$ values for the three compounds are 0.78 (0.17-2.29), 0.65 (0.034-3.31) and 0.74 (0.12-4.79) µM, respectively. The automated COMPARE analysis showed that the three compounds have similar $GI_{50}$ response patterns in the NCI 60 cancer cell lines, indicated the similar anticancer mechanism of action of the three compounds. However, when comparing the three miliusanes with the other compounds in the NCI database, we do not find similar cell killing response pattern. The COMPARE negative thus raises further interests for the development of the miliusanes as potent anticancer drug candidates with a potential unique mechanism.

Figure 4:
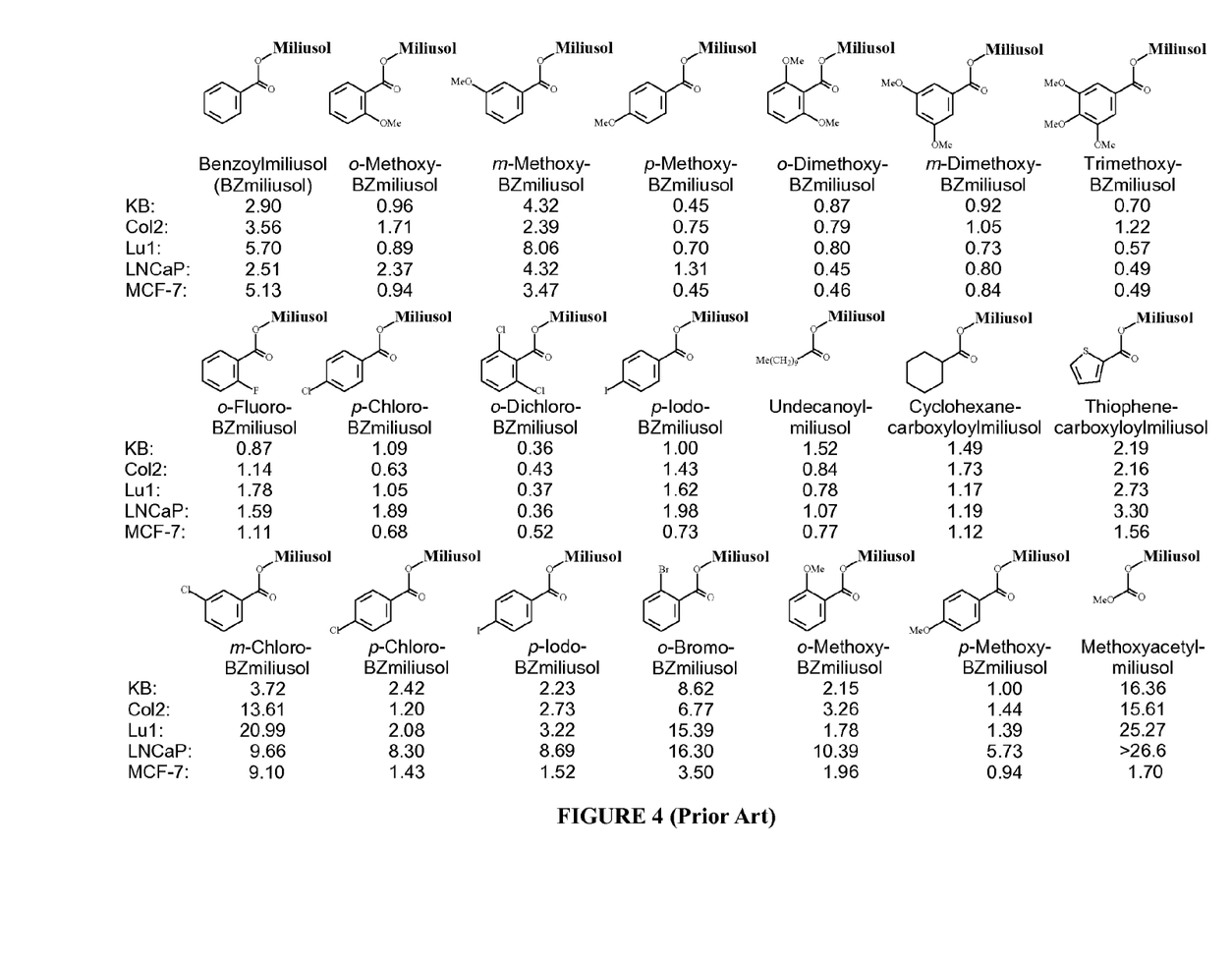
FIG. 4 shows tumor cell killing activity of miliusane derivatives (vinblastine: KB=0.00037, Lu1=0.011, Col2=0.0043, LNCaP=0.00061, MCF-7=0.0026). The results are expressed as $IC_{50}$ in μM.

In an attempt to improve the anticancer activity of miliusanes, we prepared 42 miliusane derivatives with miliusol as the starting molecule such as the compounds of formula (V). Many of the miliusol derived compounds showed equivalent activity to miliusol itself, and a number of them demonstrated superior activity to the mother molecule (see FIG. 4) (Zhang H J, Ma C Y, Hung N V, Cuong N M, Tan G T, Santarsiero B D, Mesecar A D, Soejarto D D, Pezzuto J M, Fong H H S. Miliusanes, a class of cytotoxic agents from *Miliusa sinensis*. Journal of Medicinal Chemistry 2006; 49: 693-708).

(V)

Miliusanes are considered as a group of compounds containing a substructure of oxo-spirodecane. A few patents have been published related to the compounds containing oxospirodecane or azaspirodecane or thiaspirocecane substructure (US 2009/0318548A1; US2011/021624A1 and WO2011098433A1).

In US 2009/0318548A1, the compounds of formula (VI) were synthesized. However, no anticancer data were reported in this patent.

(VI)

In US2011/021624A1, the compounds of formula (VII) were synthesized. However, the representative compound was reported to show weak cytotoxicity against MDA-MB-435, HCT116, A549 and Hela cancer cells ($IC_{50}$ values in the range of 17-42 μM).

(VII)

In WO2011098433A1, the compounds of formula (VIII) were synthesized. The compounds have a chemical structure containing a biphenyl group, and were reported to have tumor inhibition activity by inhibiting fatty acid synthesis.

(VIII)

Thus, miliusanes compounds with an improved anticancer activity and low in toxicity are needed.

Citation or identification of any reference in this section or any other section of this application shall not be construed as an admission that such reference is available as prior art for the present application.

SUMMARY OF INVENTION

The present invention relates to anticancer agents which are synthesized based on miliusane. More particularly, the agents are derivatives of the core structures of miliusanes. It is a goal of the present invention to provide miliusane derivatives having biological activity against cancer, particularly colon cancer, breast cancer, prostate cancer, lung cancer, melanoma, leukemia, brain cancer, renal cancer, ovarian cancer, and oral epidermoid cancer.

Accordingly, a first aspect of the present invention is a compound based on the core structures of miliusane for use in the treatment, prevention or delay of progression of a cancer in a patient.

A second aspect of the present invention is a pharmaceutically acceptable salt or prodrug based on the core structures of miliusane, for use in the treatment, prevention or delay of progression of a cancer in a patient.

A third aspect of the present invention is a pharmaceutical formulation comprising a compound based on the core structures of miliusane, or a pharmaceutically acceptable salt or prodrug thereof, for use in the treatment, prevention or delay of progression of a cancer in a patient.

Another aspect of the present invention concerns the use of an extract or a fraction made from plant material containing one or more miliusane compounds for use in the treatment, prevention or delay of progression of a cancer in a patient.

Compounds of the present invention may exist in different forms, such as free acids, free bases, enantiomers, racemates, diastereomers, esters and other prodrugs, salts and tautomers, and the disclosure includes all variant forms of these compounds.

The extent of protection includes counterfeit or fraudulent products which contain or purport to contain a compound of the present invention irrespective of whether they do in fact contain such a compound and irrespective of whether any such compound is contained in a therapeutically effective amount.

Included in the scope of protection are packages which include a description or instructions which indicate that the package contains a species or pharmaceutical formulation of the present invention and a product which is or comprises, or purports to be or comprise, such a formulation or species. Such packages may be, but are not necessarily, counterfeit or fraudulent.

Features, integers, characteristics, compounds, chemical moieties or groups described in conjunction with a particular aspect, embodiment or example of the present invention are to be understood to be applicable to any other aspect, embodiment or example described herein unless incompatible therewith.

Those skilled in the art will appreciate that the present invention described herein is susceptible to variations and modifications other than those specifically described.

The present invention includes all such variation and modifications. The present invention also includes all of the steps and features referred to or indicated in the specification, individually or collectively and any and all combinations or any two or more of the steps or features.

Throughout this specification, unless the context requires otherwise, the word "comprise" or variations such as "comprises" or "comprising", will be understood to imply the inclusion of a stated integer or group of integers but not the exclusion of any other integer or group of integers. It is also noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the present invention.

Furthermore, throughout the specification and claims, unless the context requires otherwise, the word "include" or variations such as "includes" or "including", will be understood to imply the inclusion of a stated integer or group of integers but not the exclusion of any other integer or group of integers.

Other definitions for selected terms used herein may be found within the detailed description of the present invention and apply throughout. Unless otherwise defined, all other technical terms used herein have the same meaning as commonly understood to one of ordinary skill in the art to which the present invention belongs.

Other aspects and advantages of the present invention will be apparent to those skilled in the art from a review of the ensuing description.

BRIEF DESCRIPTION OF DRAWINGS

The above and other objects and features of the present invention will become apparent from the following description of the present invention, when taken in conjunction with the accompanying drawings, in which.

DETAILED DESCRIPTION OF INVENTION

The present invention is not to be limited in scope by any of the specific embodiments described herein. The following embodiments are presented for exemplification only.

Definitions

Miliusane and Core Structures

The term "miliusane" as used herein includes reference to a compound comprising the basic structure shown as below:

Miliusane

The term "the core structure of miliusane" as used herein includes reference to a compound comprising the basic structure shown as below:

The Core Structure of Miliusane

In one class of the core structures of miliusane compounds, the methyl group and the ethyl group are forming a tetrahydrofuran ring (1-oxa-spiro[4.5]decane and 2-oxa-spiro[4.5]decane).

1-Oxa-spiro[4.5]decane    2-Oxa-spiro[4.5]decane In the second class of the core structures of miliusane compounds, the methyl group and the ethyl group are forming a tetrahydro-thiophene ring (1-thia-spiro[4.5]decane and 2-thia-spiro[4.5]decane).

1-Thia-spiro[4.5]decane    2-Thia-spiro[4.5]decane

In the third class of the cores structure of miliusane compounds, the methyl group and the ethyl group are forming a pyrrolidine ring (1-aza-spiro[4.5]decane, 2-aza-spiro[4.5]decane, 1-aza-spiro[4.5]dec-1-ene, 2-aza-spiro[4.5]dec-1-ene and 2-aza-spiro[4.5]dec-2-ene).

1-Aza-spiro [4.5]decane    2-Aza-spiro [4.5]decane    1-Aza-spiro [4.5]dec-1-ene 2-Aza-spiro [4.5]dec-1-ene    2-Aza-spiro [4.5]dec-2-ene Hydrocarbyl The term "hydrocarbyl" as used herein includes reference to a moiety consisting exclusively of hydrogen and carbon atoms; such a moiety may comprise an aliphatic and/or an aromatic moiety. The moiety may comprise 1, 2, 3, 4, 5, 6, 7, 8, 9, 10, 11, 12, 13, 14, 15, 16, 17, 18, 19 or 20 carbon atoms. Examples of hydrocarbyl groups include $C_{1-6}$ alkyl (e.g. $C_1$, $C_2$, $C_3$ or $C_4$ alkyl, for example methyl, ethyl, propyl, isopropyl, n-butyl, sec-butyl or tert-butyl); $C_{1-6}$ alkyl substituted by aryl (e.g. benzyl) or by cycloalkyl (e.g. cyclopropylmethyl); cycloalkyl (e.g. cyclopropyl, cyclobutyl, cyclopentyl or cyclohexyl); aryl (e.g. phenyl, naphthyl or fluorenyl) and the like.

Alkyl

The terms "alkyl" and "$C_{1-6}$ alkyl" as used herein include reference to a straight or branched chain alkyl moiety having 1, 2, 3, 4, 5 or 6 carbon atoms. This term includes reference to groups such as methyl, ethyl, propyl (n-propyl or isopropyl), butyl (n-butyl, sec-butyl or tert-butyl), pentyl, hexyl and the like. In particular, the alkyl moiety may have 1, 2, 3 or 4 carbon atoms.

Alkenyl

The terms "alkenyl" and "$C_{2-6}$ alkenyl" as used herein include reference to a straight or branched chain alkyl moiety having 2, 3, 4, 5 or 6 carbon atoms and having, in addition, at least one double bond, of either E or Z stereochemistry where applicable. This term includes reference to groups such as ethenyl, 2-propenyl, 1-butenyl, 2-butenyl, 3-butenyl, 1-pentenyl, 2-pentenyl, 3-pentenyl, 1-hexenyl, 2-hexenyl and 3-hexenyl and the like.

Alkynyl

The terms "alkynyl" and "$C_{2-6}$ alkynyl" as used herein include reference to a straight or branched chain alkyl moiety having 2, 3, 4, 5 or 6 carbon atoms and having, in addition, at least one triple bond. This term includes reference to groups such as ethynyl, 1-propynyl, 2-propynyl, 1-butyryl, 2-butynyl, 3-butynyl, 1-pentynyl, 2-pentynyl, 3-pentynyl, 1-hexynyl, 2-hexynyl and 3-hexynyl and the like.

Alkoxy

The terms "alkoxy" and "$C_{1-6}$ alkoxy" as used herein include reference to —O-alkyl, wherein alkyl is straight or branched chain and comprises 1, 2, 3, 4, 5 or 6 carbon atoms. In one class of embodiments, alkoxy has 1, 2, 3 or 4 carbon atoms. This term includes reference to groups such as methoxy, ethoxy, propoxy, isopropoxy, butoxy, tert-butoxy, pentoxy, hexoxy and the like.

Cycloalkyl

The term "cycloalkyl" as used herein includes reference to an alicyclic moiety having 3, 4, 5, 6, 7 or 8 carbon atoms. The group may be a bridged or polycyclic ring system. More often cycloalkyl groups are monocyclic. This term includes reference to groups such as cyclopropyl, cyclobutyl, cyclopentyl, cyclohexyl, norbornyl, bicyclo[2.2.2]octyl and the like.

Aryl

The term "aryl" as used herein includes reference to an aromatic ring system comprising 6, 7, 8, 9, 10, 11, 12, 13, 14, 15 or 16 ring carbon atoms. Aryl is often phenyl but may be a polycyclic ring system, having two or more rings, at least one of which is aromatic. This term includes reference to groups such as phenyl, naphthyl, fluorenyl, azulenyl, indenyl, anthryl and the like.

Cyclic Group

"Cyclic group" means a ring or ring system, which may be unsaturated or partially unsaturated but is usually saturated, typically containing 5 to 13 ring-forming atoms, for example a 5- or 6-membered ring. The ring or ring system may be substituted with one or more hydrocarbyl groups. Cyclic group includes carbocyclyl and heterocyclyl moeities.

Carbocyclyl

The term "carbocyclyl" as used herein includes reference to a saturated (e.g. cycloalkyl) or unsaturated (e.g. aryl) ring moiety having 3, 4, 5, 6, 7, 8, 9, 10, 11, 12, 13, 14, 15 or 16 carbon ring atoms. In particular, carbocyclyl includes a 3- to 10-membered ring or ring system and, in particular, 5- or 6-membered rings, which may be saturated or unsaturated. The ring or ring system may be substituted with one or more hydrocarbyl groups. A carbocyclic moiety is, for example, selected from cyclopropyl, cyclobutyl, cyclopentyl, cyclohexyl, norbornyl, bicyclo[2.2.2]octyl, phenyl, naphthyl, fluorenyl, azulenyl, indenyl, anthryl and the like.

Heterocyclyl

The term "heterocyclyl" as used herein includes reference to a saturated (e.g. heterocycloalkyl) or unsaturated (e.g. heteroaryl) heterocyclic ring moiety having from 3, 4, 5, 6, 7, 8, 9, 10, 11, 12, 13, 14, 15 or 16 ring atoms, at least one of which is selected from nitrogen, oxygen, phosphorus, silicon and sulphur. In particular, heterocyclyl includes a 3- to 10-membered ring or ring system and more particularly a 5- or 6-membered ring, which may be saturated or unsaturated. The ring or ring system may be substituted with one or more hydrocarbyl groups.

A heterocyclic moiety is, for example, selected from oxiranyl, azirinyl, 1,2-oxathiolanyl, imidazolyl, thienyl, furyl, tetrahydrofuryl, pyranyl, thiopyranyl, thianthrenyl, isobenzofuranyl, benzofuranyl, chromenyl, 2H-pyrrolyl, pyrrolyl, pyrrolinyl, pyrrolidinyl, pyrrolizidinyl, imidazolyl, imidazolidinyl, benzimidazolyl, pyrazolyl, pyrazinyl, pyrazolidinyl, thiazolyl, isothiazolyl, dithiazolyl, oxazolyl, isoxazolyl, pyridyl, pyrazinyl, pyrimidinyl, piperidyl, piperazinyl, pyridazinyl, morpholinyl, thiomorpholinyl, especially thiomorpholino, indolizinyl, isoindolyl, 3H-indolyl, indolyl, benzimidazolyl, cumaryl, indazolyl, triazolyl, tetrazolyl, purinyl, 4/V-quinolizinyl, isoquinolyl, quinolyl, tetrahydroquinolyl, tetrahydroisoquinolyl, decahydroquinolyl, octahydroisoquinolyl, benzofuranyl, dibenzofuranyl, benzothiophenyl, dibenzothiophenyl, phthalazinyl, naphthyridinyl, quinoxalyl, quinazolinyl, quinazolinyl, cinnolinyl, pteridinyl, carbazoiyl, β-carbolinyl, phenanthridinyl, acridinyl, perimidinyl, phenanthrolinyl, furazanyl, phenazinyl, phenothiazinyl, phenoxazinyl, chromenyl, isochromanyl, chromanyl and the like.

Heterocycloalkyl

The term "heterocycloalkyl" as used herein includes reference to a saturated heterocyclic moiety having 3, 4, 5, 6 or 7 ring carbon atoms and 1, 2, 3, 4 or 5 ring heteroatoms selected from nitrogen, oxygen, phosphorus and sulphur. The group may be a polycyclic ring system but more often is monocyclic. This term includes reference to groups such as azetidinyl, pyrrolidinyl, tetrahydrofuranyl, piperidinyl, oxiranyl, pyrazolidinyl, imidazolyl, indolizidinyl, piperazinyl, thiazolidinyl, morpholinyl, thiomorpholinyl, quinolizidinyl and the like. The ring or ring system may be substituted with one or more hydrocarbyl groups.

Heteroaryl

The term "heteroaryl" as used herein includes reference to an aromatic heterocyclic ring system having 5, 6, 7, 8, 9, 10, 11, 12, 13, 14, 15 or 16 ring atoms, at least one of which is selected from nitrogen, oxygen and sulphur. The group may be a polycyclic ring system, having two or more rings, at least one of which is aromatic, but is more often monocyclic. The ring or ring system may be substituted with one or more hydrocarbyl groups. This term includes reference to groups such as pyrimidinyl, furanyl, benzo[b]thiophenyl, thiophenyl, pyrrolyl, imidazolyl, pyrrolidinyl, pyridinyl, benzo[b]furanyl, pyrazinyl, purinyl, indolyl, benzimidazolyl, quinolinyl, phenothiazinyl, triazinyl, phthalazinyl, 2H-chromenyl, oxazolyl, isoxazolyl, thiazolyl, isoindolyl, indazolyl, purinyl, isoquinolinyl, quinazolinyl, pteridinyl and the like.

Halogen

The term "halogen" as used herein includes reference to F, Cl, Br or I.

Halogen Containing Moiety

The expression "halogen containing moiety" as used herein includes reference to a moiety comprising 1 to 30 plural valence atoms selected from carbon, nitrogen, oxygen and sulphur which moiety includes at least one halogen. The moiety may be hydrocarbyl for example $C_{1-6}$ alkyl or $C_{1-6}$ alkoxy, or carbocyclyl for example aryl.

Substituted

The term "substituted" as used herein in reference to a moiety means that one or more, especially up to 5, more especially 1, 2 or 3, of the hydrogen atoms in said moiety are replaced independently of each other by the corresponding number of the described substituents. The term "optionally substituted" as used herein means substituted or un-substituted. It will, of course, be understood that substituents are only at positions where they are chemically possible, the person skilled in the art being able to decide (either experimentally or theoretically) without inappropriate effort whether a particular substitution is possible.

Enantiomer

The term "enantiomer" as used herein means one of two stereoisomers that have mirror images of one another.

Racemate

The term "racemate" as used herein means a mixture of equal amounts of enantiomers of a chiral molecule.

Diastereomer

The term "diastereomer" as used herein means one of a class of stereoisomers that are not enantiomers, but that have different configurations at one or more of the equivalent chiral centers. Example of diasteromers are epimers that differ in configuration of only one chiral center.

Stereoisomer

The term "stereoisomer" as used herein means one of a class of isomeric molecules that have the same molecular formula and sequence of bonded atoms, but different three-dimensional orientations of their atoms in space.

Tautomers

The term "tautomer" means isomeric molecules that readily interconvert by a chemical reaction. The reaction commonly results in the migration of a hydrogen atom, which results in a switch of a single bond and adjacent double bond.

Prodrug

A prodrug is a medication that is administered as an inactive (or less than fully active) chemical derivative that is subsequently converted to an active pharmacological agent in the body, often through normal metabolic processes.

Independently

Where two or more moieties are described as being "each independently" selected from a list of atoms or groups, this means that the moieties may be the same or different. The identity of each moiety is therefore independent of the identities of the one or more other moieties.

Embodiments of the present invention are described below. Preferred features of each aspect of the present invention are as for each of the other aspects mutatis mutandis. Moreover, it will be appreciated that the features specified in each embodiment may be combined with other specified features, to provide further embodiments.

Compounds of the Present Invention

In an exemplary embodiment, the present invention provides compounds of formula (I), (II), (III), or (IV):

(I)

(II)

(III)

(IV)

wherein $R^1, R^2, R^3, R^4, R^5, R^6, R^7, R^8, R^9, R^{10}, R^{11}, R^{12}, R^{13}, R^{14}, R^{15}$ and $R^{16}$ are each independently selected from hydrogen, halogen or a moiety comprising 1 to 30 plural valence atoms selected from carbon, nitrogen, oxygen and sulphur; or these groups may be taken together with the carbon atoms to which they are attached to form one or more cyclic groups which is optionally substituted with halogen or a moiety comprising 1 to 30 plural valence atoms selected from carbon, nitrogen, oxygen and sulphur; $R^1$ and $R^2$, $R^3$ and $R^4$, $R^5$ and $R^6$, $R^7$ and $R^8$, $R^9$ and $R^{10}$, $R^{11}$ and $R^{12}$, $R^{13}$ and $R^{14}$ or $R^{15}$ and $R^{16}$ may be taken together with the carbon atoms to which they are attached to form one or more carboxyl groups (C=O); or while one of $R^1$ and $R^2$, $R^3$ and $R^4$, $R^5$ and $R^6$, $R^7$ and $R^8$, $R^9$ and $R^{10}$, $R^{11}$ and $R^{12}$, $R^{13}$ and $R^{14}$ or $R^{15}$ and $R^{16}$ is hydrogen, halogen, hydrocarbyl or alkoxy, the other one of $R^1$ and $R^2$, $R^3$ and $R^4$, $R^5$ and $R^6$, $R^7$ and $R^8$, $R^9$ and $R^{10}$, $R^{11}$ and $R^{12}$, $R^{13}$ and $R^{14}$ or $R^{15}$ and $R^{16}$ is selected from $R^{17}$, —$OR^{17}$, —$C(O)R^{17}$ and —$C(O)OR^{17}$; $R^{17}$ is independently selected from hydrogen, halogen, trifluoromethyl, cyano, nitro, hydrocarbyl optionally substituted with 1, 2, 3, 4 or 5 R$^{18}$, —(CH$_2$)$_k$-heterocyclyl optionally substituted with 1, 2, 3, 4 or 5 R$^{18}$, —OR$^{19}$, —C(O)R$^{20}$, —C(O)N(R$^{19}$)R$^{20}$, C(O)OR$^{19}$, —OC(O)R$^{19}$, —S(O)$_2$R$^{19}$, —S(O)$_2$N(R$^{19}$)R$^{20}$, —N(R$^{19}$)R$^{20}$, —N(R$^{19}$)N(R$^{19}$)R$^{20}$, —N(R$^{19}$)C(O)R$^{20}$ and —N(R$^{19}$)S(O)$_2$R$^{20}$; wherein k is an integer between 1 and 6 (e.g. 1, 2 or 3); R$^{18}$ is independently selected from halogen, trifluoromethyl, cyano, nitro, oxo, =NR$^{19}$, —OR$^{19}$, —C(O)R$^{20}$, —C(O)N(R$^{19}$)R$^{20}$, —C(O)OR$^{19}$, —OC(O)R$^{20}$, —S(O)$_2$R$^{19}$, —S(O)$_2$N(R$^{19}$)R$^{20}$, —N(R$^{19}$)R$^{20}$, —N(R$^{19}$)N(R$^{19}$)R$^{20}$, —N(R$^{19}$)C(O)R$^{20}$ and —N(R$^{19}$)S(O)$_2$R$^{20}$; R$^{19}$ and R$^{20}$ are each independently hydrogen or selected from hydrocarbyl and —(CH$_2$)$_k$-heterocyclyl, either of which is optionally substituted with 1, 2, 3, 4 or 5 substituents independently selected from halogen, cyano, amino, hydroxy, C$_{1-6}$ alkyl and C$_{1-6}$ alkoxy; wherein k is an integer between 1 and 6 (e.g. 1, 2 or 3); X is oxygen or sulphur; R is hydrogen or selected from hydrocarbyl and —(CH$_2$)$_k$-heterocyclyl, either of which is optionally substituted with 1, 2, 3, 4 or 5 substituents independently selected from halogen, cyano, amino, hydroxy, C$_{1-6}$ alkyl and C$_{1-6}$ alkoxy; wherein k is an integer between 1 and 6 (e.g. 1, 2 or 3); dashed line "----" denotes a single or double bond; or an enantiomer thereof; or a pharmaceutically acceptable salt or prodrug thereof.

It should be noted that compounds having one of the following formulae should not be the compound of the present invention and should be removed from the compound of the present invention or from the plant extract which the compound of the present invention is isolated:

Miliusate

Miliusol

Miliusane I

Miliusane II

Miliusane III

Miliusane IV

Miliusane V

Miliusane VI

Miliusane VII

Miliusane VIII

Miliusane IX

Miliusane X/XI

Miliusane XII/XIII

Miliusane XIV/XV

Miliusane XVI

Miliusane XVII

Methoxyacetyl-miliusol n-Hexanoyl-miliusol

Undecanoyl-miliusol

Cyclopropanecarbonyl-miliusol

Cyclobutanecarbonyl-miliusol

-continued

Cyclopentanecarbonyl-miliusol

Cyclohexanecarbonyl-miliusol

2-Thiophenecarbonyl-miliusol wherein Ac is acetyl group ($CH_3C=O$), and Me is methyl group ($CH_3$);

Compounds having the following formula (V):

(V)

wherein $R^1=R^2=R^3=R^4=R^5=H$; or
$R^1=R^2=R^3=R^4=H$, $R^5=OCH_3$; or
$R^1=R^3=R^4=R^5=H$, $R^2=OCH_3$; or
$R^1=R^2=R^4=R^5=H$, $R^3=OCH_3$; or $R^1=R^2=R^4=H$, $R^3=R^5=OCH_3$; or $R^1=R^5=OCH_3$, $R^2=R^3=R^4=H$; or $R^1=R^4=R^5=H$, $R^2=R^3=OCH_3$; or $R^1=R^3=R^5=H$, $R^2=R^4=OCH_3$; or $R^1=R^5=H$, $R^2=R^3=R^4=OCH_3$; or $R^1=R^4=R^5=H$, $R^2$ and $R^3$ taken together with the carbon atoms to which they are attached to form a cyclic[1,3]dioxole group; or $R^1=R^2=R^3=R^4=H$, $R^5=CH_3$; or $R^1=R^3=R^4=R^5=H$, $R^2=CH_3$; or $R^1=R^2=R^4=R^5=H$, $R^3=CH_3$; or $R^1=R^2=R^3=R^4=H$, $R^5=F$; or $R^1=R^3=R^4=R^5=H$, $R^2=F$; or $R^1=R^2=R^4=R^5=H$, $R^3=F$; or $R^1=R^2=R^3=H$, $R^4=R^5=F$; or $R^1=R^2=R^4=H$, $R^3=R^5=F$; or $R^1=R^3=R^4=H$, $R^2=R^5=F$; or $R^1=R^5=F$, $R^2=R^3=R^4=H$; or $R^1=R^4=R^5=H$, $R^2=R^3=F$; or $R^1=R^3=R^5=H$, $R^2=R^4=F$; or $R^1=R^2=R^3=R^4=H$, $R^5=Cl$; or $R^1=R^3=R^4=R^5=H$, $R^2=Cl$; or $R^1=R^2=R^4=R^5=H$, $R_3=Cl$; or $R^1=R^2=R^4=H$, $R^3=R^5=Cl$; or $R^1=R^5=Cl$, $R^2=R^3=R^4=H$; or $R^1=R^4=R^5=H$, $R^2=R^3=Cl$; or $R^1=R^3=R^5=H$, $R^2=R^4=Cl$; or $R^1=R^2=R^3=R^4=H$, $R^5=Br$; or $R^1=R^3=R^4=R^5=H$, $R^2=Br$; or $R^1=R^2=R^4=R^5=H$, $R^3=Br$; or $R^1=R^2=R^3=R^4=H$, $R^5=I$; or $R^1=R^2=R^4=R^5=H$, $R^3=I$;

Compounds having the following formula (VI):

$$\text{(VI)}$$

wherein $X^1$ and $X^2$ are carbon atoms either joined by double bond or joined by a single bond constituents of an epoxide ring or a hydroxyethylene moiety; $X^3$ and $X^4$ are carbon atoms either joined by double bond or joined by a single bond constituents of an epoxide ring or a hydroxyethylene moiety; $R^1$ is selected from the group consisting of branched alkyl chains, unbranched alkyl chains, cycloalkyl groups, aromatic groups, alcohols, ethers, amines, and substituted or unsubstituted ureas, esters, aldehydes and carboxylic acids; $R^2$ is selected from the group consisting of H, OH and $NHR^3$, wherein $R^3$ is a nitrogen protecting group;

Compounds having the following formula (VII):

(VII)

wherein $R^1$, $R^3$ and $R^4$ are selected from the group consisting of branched alkyl chains, unbranched alkyl chains, cycloalkyl groups, aromatic groups, alcohols, ethers, amines, and substituted or unsubstituted ureas, esters, aldehydes and carboxylic acids; m is an integer between 0 and 5;

Compounds having the following formula (VIII):

(VIII)

wherein Z is oxygen or sulphur or nitrogen substituted with D group; D represents hydrogen or represents a $C_1$-$C_6$-alkyl or $C_1$-$C_6$-alkoxy-$C_1$-$C_6$-alkyl radical or represents a $C_3$-$C_7$-cycloalkyl or 4- to 7-membered monocyclic heterocyclyl radical, where the radicals mentioned may optionally be mono- or polysubstituted by identical or different substituents selected from the group consisting of halogen and hydroxyl and $C_1$-$C_3$-alkyl, halo-$C_1$-$C_3$-alkyl, or $C_1$-$C_3$-alkoxy; X represents halogen, nitro or cyano or represents an optionally monohalogen- or polyhalogen-substituted $C_1$-$C_6$-alkyl, $C_1$-$C_6$-alkoxy, $C_1$-$C_6$-alkoxy-$C_1$-$C_6$-alkoxy, $C_3$-$C_7$-cycloalkyl or a $C_3$-$C_7$-cycloalkyl-$C_1$-$C_6$-alkoxy radical, and W and Y independently of one another represent hydrogen, nitro, cyano or halogen or represent an optionally monohalogen- or polyhalogen-substituted $C_1$-$C_6$-alkyl, $C_1$-$C_6$-alkoxy or $C_3$-$C_7$-cycloalkyl radical, and $V^1$, $V^2$ and $V^3$ independently of one another represent hydrogen, halogen, nitro or cyano or represent a $C_1$-$C_6$-alkyl, halo-$C_1$-$C_6$-alkyl, $C_1$-$C_6$-alkoxy, halo-$C_1$-$C_6$-alkoxy, $C_1$-$C_6$-alkylthio, $C_1$-$C_6$-alkylsulphinyl, $C_1$-$C_6$-alkylsulphonyl, $C_1$-$C_6$-alkoxy-$C_1$-$C_6$-alkyl, $C_3$-$C_{10}$-cycloalkyl radical or represent a monocyclic heterocycloalkyl radical, and/or

$V^1$ and $V^2$ together with the carbon atoms to which they are attached form a saturated or unsaturated cycle $T^1$ which optionally contains at least one further heteroatom and has 4 to 7-ring atoms and whose ring-forming atoms may be mono- or polysubstituted by identical or different substituents selected from the group consisting of halogen and a $C_1$-$C_6$-radical.

Examples of the compounds of the present invention include those shown below. It will of course be appreciated that, where appropriate, each compound may be in the form of the free compound, an enantiomer, an acid or base addition salt, or a prodrug.

In order to develop anticancer agents which are amenable to become therapeutic candidates with a potentially novel anticancer mechanism of action, two exemplary examples of the compound of the present invention are synthesized, namely N-methyl-2-pyrrolecarboxyl-miliusol and p-dimethyl-benzyol-miliusol, which show potent cancer killing activity against a panel of cancer cell lines. The chemical formulae of the exemplary examples of the compound are as follows:

N-Methyl-2-pyrrolecarboxyl-miliusol p-Dimethylamino-benzyol-miliusol

EXAMPLES

Plant Materials. The leaves and stems of *Miliusa balansae* Finet & Gagnep. (Annonaceae) was collected from Guizhou Province, China. As a result, the miliusane compounds, miliusol, miliusate and miliusane I are isolated from this plant.

Miliusol

Miliusate

-continued

Miliusane I

N-Methyl-2-pyrrolecarboxyl-miliusol

Extraction and Isolation. The dried and milled leaves and stems (10 kg) of *Miliusa sinensis* are extracted with methanol (MeOH) to afford an extract, which is subsequently defatted with n-hexane and partitioned with $CHCl_3$. Separation of the $CHCl_3$-soluble fraction by column chromatography on Si gel and RP-18 Si gel columns led to the isolation of miliusol (3.73 g), miliusate (5.28 g) and miliusane I (0.31 g).

The obtained miliusol, miliusate and miliusane I will be used to prepare miliusane derivatives.

General Method for Preparation of Miliusol Ester Derivatives. The solution of 5.0 mg of miliusane (0.016 mmol) in 1.0 mL of dry pyridine is pipetted into a solution of selected acyl chloride reagent such as p-dimethyl-benzyol chloride and N-methyl-2-pyrrolecarboxyl chloride (0.2 mmol) in 1.0 mL of dry pyridine at 0° C. The reaction is allowed to proceed at 0° C. for 2 hrs, and additional 20 hrs at room temperature. The reaction product is evaporated in vacuo to dryness to afford a mixture, which is subjected to a Si gel column separation to afford acyl-miliusane ester. Unreacted, partially reacted or unwanted compounds as disclosed herein should be removed from the reaction product.

SCHEME 1

Miliusol

N-Methyl-2-pyrrole-carboxyl chloride pyridine
room temperature

SCHEME 2

Miliusol p-Dimethyl-benzoyl chloride pyridine
room temperature p-Dimethylamino-benzyol-miliusol The new molecules N-methyl-2-pyrrolecarboxyl-miliusol and p-dimethyl-benzyol-miliusol are thus synthesized (see Schemes 1 and 2). The compounds are demonstrated to have potent cell killing activity against the human cancer cell lines KB, HCT116, LNCaP, A549 and MCF-7 with $IC_{50}$ values ranging from 0.1-1.5 μM, which are more potent than the parent compound miliusol in term of cancer cell killing activity.

N-Methyl-2-pyrrolecarboxyl-miliusol p-Dimethylamino-benzyol-miliusol

N-methyl-2-pyrrolecarboxyl-miliusol is obtained as a white powder with a molecular formula of $C_{24}H_{29}NO_5$ determined by positive HRESIMS and NMR studies. $^1H$ NMR (400 MHz, $CDCl_3$, J in Hz) δ pyrrolecarboxyl protons [6.94 (1H, dd, J=4.0, 1.8), 6.85 (1H, brt, J=2.0), 6.12 (1H, dd, J=4.0, 2.5)], 6.89 (1H, ddd, J=10.2, 3.9, 0.9, H-4), 6.08 (1H, dd, J=10.2, 1.3, H-3), 5.69 (1H, brdtd, J=5.3, 4.0, 1.2, H-5), 5.54 (1H, d, J=10.0, H-1'), 5.14 (1H, brd, J=10.0, H-2'), 4.98 (1H, brt, J=6.5, H-6'), 3.94 (3H, s, N—$CH_3$), 3.37 (1H, d, J=17.6, H-7β), 2.50 (1H, ddd, J=14.7, 4.0, 0.9, H-6β), 2.29 (1H, dd, J=14.7, 5.6, H-6α), 2.26 (1H, d, J=17.5, H-7α), 2.03 (2H, m, $H_2$-5'), 1.99 (2H, m, $H_2$-4'), 1.69 (3H, d, J=1.3, $CH_3$-9'), 1.66 (3H, s, $CH_3$-8'), 1.56 (3H, s, $CH_3$-10').

p-Dimethylamino-benzoyl-miliusol is obtained as a white powder with a molecular formula of $C_{27}H_{33}NO_5$ determined by positive HRESIMS and NMR studies. $^1H$ NMR (400 MHz, $CDCl_3$, J in Hz) δ dimethylamino-benzyol protons [7.89 (2H, d, J=8.7), 6.68 (2H, m)], 6.96 (1H, brdd, J=10.1, 3.7, H-4), 6.08 (1H, d, J=10.1, H-3), 5.74 (1H, m, H-5), 5.58 (1H, d, J=10.0, H-1'), 5.16 (1H, brd, J=9.9, H-2'), 4.98 (1H, brt, J=6.5, H-6'), 3.37 (1H, d, J=17.6, H-7β), 3.05 [(6H, s, N—$(CH_3)_2$], 2.53 (1H, brdd, J=14.3, 3.9, H-6β), 2.33 (1H, dd, J=14.0, 5.6, H-6α), 2.28 (1H, d, J=17.6, H-7α), 2.02 (2H, m, $H_2$-5'), 1.99 (2H, m, $H_2$-4'), 1.66 (6H, s, $CH_3$-8' and $CH_3$-9'), 1.56 (3H, s, $CH_3$-10').

Cell Culture Panel Bioassays. All pure compounds of the present invention are evaluated against the human cancer cell lines comprising a cytotoxicity screening panel. Cytotoxicity assays involving oral epidermoid (KB), colon (HCT116), prostate (LNCaP), breast (MCF-7) and lung (A549) carcinoma cell lines, are performed using sulforhodamine B according to established protocols (Zhang H J, Ma C Y, Hung N V, Cuong N M, Tan G T, Santarsiero B D, Mesecar A D, Soejarto D D, Pezzuto J M, Fong H H S. Miliusanes, a class of cytotoxic agents from *Miliusa sinensis*. Journal of Medicinal Chemistry 2006; 49: 693-708; and Jutiviboonsuk A, Zhang H J, Tan G T, Ma C M, Hung N V, Cuong N M, Bunyapraphatsara N, Soejarto D D, Fong H H S. Bioactive constituents from the roots of *Bursera tonkinensis*. Phytochemistry 2005; 66: 2745-2751.). KB cells are maintained in DMEM medium. LNCaP cells are maintained in RPMI1640 medium with hormone-free 10% heat-activated FBS (fetal bovine serum) supplemented with 0.1 nM testosterone. MCF-7 cells are maintained and assayed in MEME medium containing 10 mg/L of insulin. HCT116 cells are maintained in McCoy's 5A medium supplemented with 10% fetal bovine serum. A549 cells are maintained in RPMI-1640 medium supplemented with 10% FCS. Serial dilutions of the compounds are prepared using 10% aqueous DMSO as solvent. The 190 μL cell suspension ($3\times10^4$ cells in 1 ml media) is incubated with 10 μL sample solutions, in triplicate, in 96-well tissue culture plate at 37° C. in a humidified atmosphere of 5% $CO_2$ in air for 72 hours. 10 μL 10% aqueous DMSO is used as control group. Then the cells are fixed to plastic substratum by the addition of 100 μL cold 20% aqueous trichloroacetic acid and washing with water after incubation at 4° C. for 30 min. After staining cells with 100 μL of 0.4% sulforhodamine B in 1% aqueous AcOH for 30 min, unbound dye is removed by rinsing with 1% aqueous AcOH. The bound dye is solubilized with 200 μL 10 mM unbuffered Tris base, pH 10, and the optical density is measured at 515 nm using an ELISA plate reader. The average data are expressed as a percentage, relative to the control. The $IC_{50}$ values, the dose that inhibit cell growth by 50%, are calculated using nonlinear regression analysis (percent survival versus concentration).

Having now fully described the present invention in some detail by way of illustration and examples for purposes of clarity of understanding, it will be obvious to one of ordinary skill in the art that the same can be performed by modifying or changing the present invention within a wide and equivalent range of conditions, formulations and other parameters without affecting the scope of the present invention or any specific embodiment thereof, and that such modifications or changes are intended to be encompassed within the scope of the appended claims. The terms and expressions which have been employed are used as terms of description and not of limitation, and there is no intention that in the use of such terms and expressions of excluding any equivalents of the features shown and described or portions thereof, but it is recognized that various modifications are possible within the scope of the present invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of the present invention.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms.

When a group of materials, compositions, components or compounds is disclosed herein, it is understood that all individual members of those groups and all subgroups thereof are disclosed separately. When a Markush group or other grouping is used herein, all individual members of the group and all combinations and subcombinations possible of the group are intended to be individually included in the disclosure. Every formulation or combination of components described or exemplified herein can be used to practice the present invention, unless otherwise stated. Whenever a range is given in the specification, for example, a temperature range, a time range, or a composition range, all intermediate ranges and subranges, as well as all individual values included in the ranges given are intended to be included in the disclosure. In the disclosure and the claims, "and/or" means additionally or alternatively. Moreover, any use of a term in the singular also encompasses plural forms.

All references cited herein are hereby incorporated by reference in their entirety to the extent that there is no inconsistency with the disclosure of this specification. Some references provided herein are incorporated by reference to provide details concerning sources of starting materials, additional starting materials, additional reagents, additional methods of synthesis, additional methods of analysis, additional biological materials, additional cells, and additional uses of the present invention. All headings used herein are for convenience only. All patents and publications mentioned in the specification are indicative of the levels of skill of those skilled in the art to which the present invention pertains, and are herein incorporated by reference to the same extent as if each individual publication, patent or patent application was specifically and individually indicated to be incorporated by reference. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

If desired, the different functions discussed herein may be performed in a different order and/or concurrently with each other. Furthermore, if desired, one or more of the above-described functions may be optional or may be combined.

While the foregoing invention has been described with respect to various embodiments and examples, it is understood that other embodiments are within the scope of the present invention as expressed in the following claims and their equivalents. Moreover, the above specific examples are to be construed as merely illustrative, and not limitative of the reminder of the disclosure in any way whatsoever. Without further elaboration, it is believed that one skilled in the art can, based on the description herein, utilize the present invention to its fullest extent. All publications recited herein are hereby incorporated by reference in their entirety.

INDUSTRIAL APPLICABILITY

The present invention discloses new anticancer agents based on the miliusane natural products. The present invention also includes its preparation and application method for treating cancer.

What is claimed is:

1. A compound comprising the following formula (I):

(I)

wherein $R^1$ and $R^2$ are independently substituted by hydrogen, or taken together with the carbon atoms to which they are attached to form a carboxyl group (C=O);

$R^3$ and $R^4$ are independently substituted by hydrogen, hydroxy, or taken together with the carbon atoms to which they are attached to form a carboxyl group (C=O);

$R^5$ and $R^6$ are each independently substituted by hydrogen, hydroxy, or taken together with the carbon atoms to which they are attached to form a carboxyl group (C=O);

each pair of the substituted groups $R^7$ and $R^8$, $R^9$ and $R^{10}$, or $R^{11}$ and $R^{12}$ is independently taken together with the carbon atoms to which they are attached to form one or more carboxyl groups (C=O); or while one substituent of $R^7$ and $R^8$, one substituent of $R^9$ and $R^{10}$, or one substituent of $R^{11}$ and $R^{12}$ is hydrogen or halogen whereas the other substituent of $R^7$ and $R^8$, the other substituent of $R^9$ and $R^{10}$, or the other substituent of $R^{11}$ and $R^{12}$ is selected from —$OR^{17}$;

$R^{13}$ and $R^{14}$ are independently substituted by hydrogen, hydroxy, or taken together with the carbon atoms to which they are attached to form a carboxyl group (C=O);

$R^{15}$ and $R^{16}$ are independently substituted by hydrogen, or hydrocarbyl, wherein said hydrocarbyl has at least seven carbons and one carbon-carbon double bond (C=C), and may be optionally substituted with one, two, or three substituents independently selected from hydroxy, C1-6 alkyl or C1-6 alkoxy;

$R^{17}$ is selected from $R^{18}$, —$C(O)R^{18}$ and —$C(O)N(R^{19})R^{20}$;

$R^{18}$ is selected from heterocyclyl, hydrocarbyl and —$(CH_2)_k$-heterocyclyl, wherein the hydrocarbyl is substituted with one, two, three, four or five of $R^{21}$; the heterocyclyl or —$(CH_2)_k$-heterocyclyl is substituted with one, two, three, four or five of $R^{21}$ and; when the heterocyclyl or —$(CH_2)_k$-heterocyclyl has at least one nitrogen in ring thereof, the heterocyclyl or -$(CH_2)_k$-heterocyclyl is unsubstituted or independently substituted with one, two, three, four or five of substituents selected from $R^{21}$ and alkyl; wherein k is an integer between 1 and 6;

$R^{19}$ and $R^{20}$ are independently selected from hydrogen, or $C_{1-6}$ alkyl;

$R^{21}$ is selected from —$N(R^{19})R^{20}$;

X is oxygen;

dashed line denotes a single or double bond;

said compound further comprising a pharmaceutically acceptable salt or prodrug thereof.

2. The compound of claim 1, wherein said compound is an optically pure stereoisomer.

3. The compound of claim 1, wherein said compound is an enantiomer.

4. The compound of claim 1, wherein said compound is a racemate.

5. The compound of claim 1, wherein said compound is a diastereomer.

6. The compound of claim 1, wherein said compound is a tautomer.

7. A pharmaceutical composition comprising an effective amount of the compound of claim 1 and a pharmaceutically acceptable carrier thereof.

8. The compound of claim 1 is selected from N-methyl-2-pyrrolecarboxyl-miliusol or p-dimethyl-benzyol-miliusol with the following formulae respectively:

N-Methyl-2-pyrrolecarboxyl-miliusol p-Dimethylamino-benzyol-miliusol or a pharmaceutically acceptable salt or prodrug thereof.

9. A method of treating a cancer comprising administering the compound of claim 1 to a subject in needs thereof, wherein said cancer comprising colon cancer, breast cancer, prostate cancer, lung cancer, or oral epidermoid cancer.

10. The method of claim 9, wherein said subject is a human.

* * * * *